(12) United States Patent
Jensen et al.

(10) Patent No.: US 6,312,413 B1
(45) Date of Patent: Nov. 6, 2001

(54) CYLINDER AMPOULE

(75) Inventors: Jens Møller Jensen, Copenhagen; Thomas Buch-Rasmussen, Gentofte; Jens Ulrik Poulsen, Virum, all of (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/176,581

(22) Filed: Oct. 21, 1998

Related U.S. Application Data

(60) Provisional application No. 60/064,743, filed on Nov. 7, 1997.

(30) Foreign Application Priority Data

Oct. 30, 1997 (DK) .................................................. 1236/97

(51) Int. Cl.⁷ ..................................................... A61M 5/00
(52) U.S. Cl. ............................................ 604/232; 604/211
(58) Field of Search .............................. 604/232, 89, 187, 604/218, 228, 207, 208, 211

(56) References Cited

U.S. PATENT DOCUMENTS

| | | | |
|---|---|---|---|
| 2,736,315 | * 2/1956 | Feeny | 128/218 |
| 3,563,240 | * 2/1971 | Silver | 128/234 |
| 4,275,729 | * 6/1981 | Silver et al. | 128/218 |
| 4,563,174 | * 1/1986 | Dupont et al. | 604/89 |
| 5,108,378 | 4/1992 | Firth et al. | 604/192 |
| 5,445,618 | 8/1995 | Adobatti | 604/192 |

FOREIGN PATENT DOCUMENTS 2108381 8/1972 (DE) .

* cited by examiner

*Primary Examiner*—Sharon Kennedy
*Assistant Examiner*—Catherine Serke
(74) *Attorney, Agent, or Firm*—Skadden, Arps, Slate, Meager & Flom LLP

(57) ABSTRACT

A cylinder ampoule (1) having a first end sealed by a closure through which an injection unit can communicate with a medicament in the ampoule and a second end closed by a piston (3) which can be forced into the ampoule (1) to press out a dose of a medicament stored in the ampoule between the closure and the piston (3) through said injection unit, which cylinder ampoule (1) has a non-circular inner cross section and which piston (3) has a non-circular cross section corresponding to the inner cross section of the ampoule (1). A piston rod (4) has a pressure foot (5) which has a cross section corresponding to the inner cross section of the ampoule (1) and is non-rotatably connected to the piston rod (4).

5 Claims, 1 Drawing Sheet

CYLINDER AMPOULE

CROSS-REFERENCE TO RELATED APPLICATIONS

Figure 1:
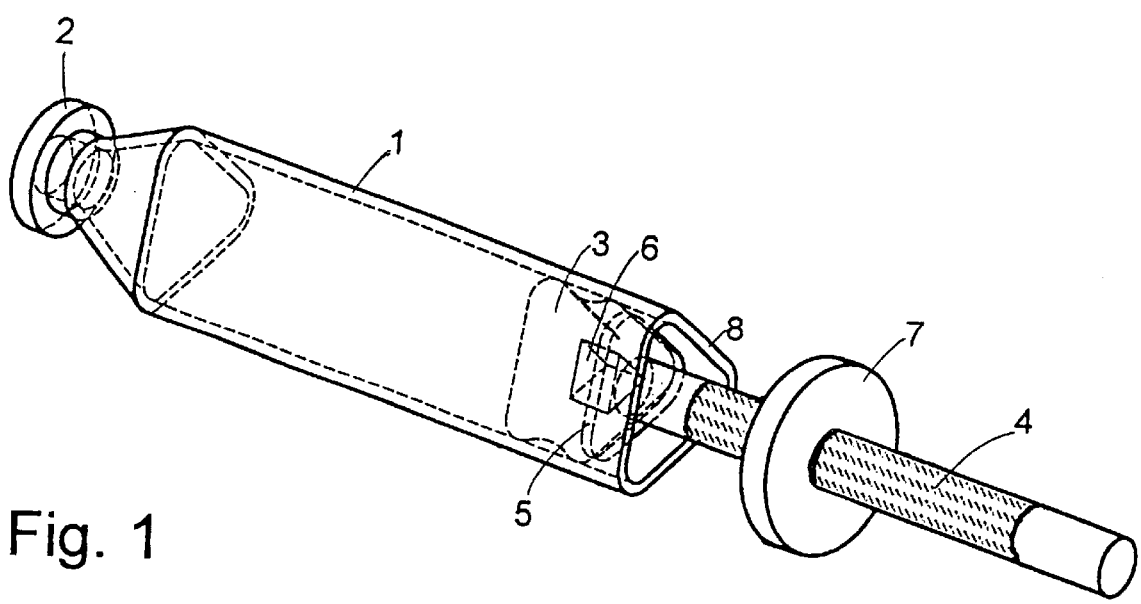

This application claims priority under 35 U.S.C. 119 of Danish application 1236/97 filed Oct. 30, 1997 and U.S. Provisional application No. 60/064,743 filed Nov. 7, 1997, the contents of which are fully incorporated herein by reference.

BACKGROUND OF THE INVENTION

The invention relates to cylinder ampoules having a first end sealed by a closure through which an injection unit can communicate with a medicament in the ampoule and a second end closed by a piston which can be forced into the ampoule to press out a dose of a medicament stored in the ampoule between the closure and the piston through said injection unit.

It shall be noticed that a cylinder is defined as a surface described when a line, the generatrix, with a defined orientation in space is moved along a guiding curve. What colloquially is called a cylinder is a so-called right circular cylinder, i.e. a cylinder whose guiding curve is a circle and whose generatrix is a line perpendicular to the plane of said circle. When talking about cylinder ampoules the word cylinder should be interpreted in the widest sense of the word although cylinder ampoules known so far are of the kind corresponding to the colloquial interpretation of the word cylinder.

Cylinder ampoules may be designed for use in syringes which are e.g. used by diabetics for the injection of insulin. Some insulin types are suspended in a liquid and the ampoule has to be shaken, rotated and turned upside down for some time to re-establish the suspension of the insulin crystals which will form a sediment when the ampoule is not in use. In a common cylinder ampoule having a circular cross-section perpendicular to its axis rotating of the ampoule will only result in a rotation of the ampoule and its content as a whole when the rotation of the ampoule is stopped, the liquid body will continue its rotation and the outer part of the rotating liquid body will break away some of the crystals which have segregated on the inner wall of the ampoule and suspend them in the said outer part of the rotating liquid body, but a homogeneous suspension where the concentration of crystals are equally suspended in the outer part and the part near the axis is difficult to obtain. Alternatively the ampoule may rotate without immediately drawing the liquid body with it. Also in this case a suspension of the segregated crystals in the outer part of the liquid body may be obtained when the ampoule wall moves relative to the liquid body but also in this case a homogeneous suspension is difficult to obtain.

From EP 235 691 it is known to place in the ampoule one or more mixing bodies in the shape of balls made from a material having a density which is different from the liquid. When the ampoule is rotated the balls will run along the wall and loosen crystals sediments. However, the balls may have a grinding effect on the crystals which may then be deactivated.

BACKGROUND OF THE INVENTION

It is an object of the invention to provide an ampoule in which sediments can be re-suspended without the use of mixing bodies.

This is obtained by an ampoule of the kind described in the opening of this application which ampoule according to the invention has a non-circular inner cross section and the piston has a non-circular cross section corresponding to the inner cross section of the ampoule.

In known syringes, the piston is pressed into the ampoule by a piston rod which acts on the piston directly or through a pressure foot, the piston rod being non-rotatable but axially displaceable in the syringe. Many dose setting devices are based on engaging threads on the piston rod and a dose setting member, respectively, and a dose is set by rotating the dose setting member relative to the piston rod.

By way of example EP 327 910 discloses a device by which doses may be set by increasing the total length of a piston rod, which abuts a piston of an ampoule in the device, and a piston rod extension which is through a threaded connection coupled to the piston rod. The increase is obtained by rotating the piston rod extension relative to the piston rod by rotating a dose setting member which can be rotated relative to the housing and consequently relative to the piston rod. A connection between the dose setting member and the piston rod extension makes the piston rod extension follow the rotation of the dose setting member. By the resulting increase of the total length of the piston rod and its extension, the outer end of the piston rod extension which was previously flush with the end of the housing is passed out through the end of the housing. The projecting end of the piston rod extension is used as an injection button which can be pressed until it again is flush with the housing. Thereby the piston is pressed into the ampoule a distance corresponding to the set increase of the total length of the piston rod and the piston rod extension.

By such dose setting devices the piston rod must be secured against rotation relative to the housing of the syringe so that the rotation of the dose setting member relative to the piston rod may be performed by holding the house of the syringe and rotate the dose setting member relative to this housing and consequently relative to the piston rod.

This securing of the piston rod against rotation relative to the housing is commonly obtained by using a piston rod which has a non-circular cross section and which passes through a conforming guiding opening through a guiding element secured to the housing.

In a cylinder ampoule according to the invention, the piston has a cross-section corresponding to the inner cross-section of the ampoule and as this cross-section is not circular it is ensured that the piston cannot be rotated relative to said housing.

According to the invention this requirement may be complied with by providing the piston rod with a pressure foot which has a cross section corresponding to the inner cross section of the ampoule and is non-rotatably connected to the piston rod.

In another embodiment the piston rod may be secured non-rotatably to the piston.

A cylinder ampoule according to the invention may form a syringe housing and the piston rod may be threaded to form a part of a dose setting mechanism.

In the following detailed description, the invention is explained in further detail with reference to the drawing.

BRIEF DESCRIPTION OF THE VIEW OF THE DRAWING

FIG. 1 is a perspective view showing, in schematic form, a cylinder ampoule according to the invention with a non-circular cross section and with a piston having a corresponding non-circular cross section.

DETAILED DESCRIPTION OF THE INVENTION

An ampoule 1 has a triangular cross section. At one end the ampoule is provided with a neck part with a flange 2. A rubber membrane seals this end of the ampoule. The other end of the ampoule is closed by a piston 3 having a cross section corresponding to the inner cross section of the ampoule.

The cross section of the ampoule must not be circular. A triangular shape is by way of example, and in principle any non-circular cross section can be chosen. It must be noticed that a cross section of a cylinder means a section perpendicular to the generatrixces of the cylinder.

A threaded piston rod 4 acts on the piston 3 through a pressure foot 5 which may be integral with the piston rod or secured to this piston rod 4 in a way making the piston rod non-rotatable relative to the pressure foot 5. The pressure foot 5 is sketched as having a cross section corresponding to the cross section of the piston 3 and the inner cross section of the ampoule 1. This way the piston rod is made inrotatable relative to the piston 3. The piston 3 is provided with a recess 6 having a triangular cross section. In this recess a piston rod provided with an end part having a corresponding triangular cross section may be inserted so that the piston rod is non-rotatably secured to the piston without any intermediate pressure foot.

A nut 7 is screwed onto the threaded piston rod and may be rotated relative to this piston rod 4 which is kept inrotatable by the ampoule. If the nut is originally abutting an end edge 8 of the ampoule, a dose may be set by screwing the nut 7 away from said edge 8 and the dose may be injected by pressing the piston rod 4 so far into the ampoule that the nut 7 again abuts the edge 8. This dose setting mechanism is independent of the housing the ampoule is mounted into and in fact no special housing is needed as the ampoule with the piston and the piston rod in itself may form a disposable syringe by which a number of doses may be set and injected. Only a needle receiving piece has to be provided at the neck end of the ampoule so that a needle hub with an injection needle communicating with the medicine in the ampoule may be mounted. Alternatively the described elements could be part of a more comprehensive mechanism serving the same purpose: Injection of a medicine.

In the above example a cylinder ampoule with a triangular cross-section is described. The cylinder may have another polygonal cross-section, an elliptic cross-section, or a cross section having combinations of straight lines and curves, without deviating from the scope of the invention, the only condition being that the cross-section is not circular.

What is claimed is:

1. A device for dispensing a medicament comprising:

a cylinder ampoule having first and second ends, wherein the first end is sealed by a closure through which an injection unit can communicate with a medicament contained in the ampoule, wherein at least a portion of the ampoule has an interior with a non-circular cross section, wherein the ampoule includes a piston having a non-circular cross section, corresponding to the non-circular interior portion of the ampoule, which is disposed in the non-circular interior portion, between the first and second ends to form a seal, and wherein the piston can be forced into the ampoule to press out a dose of a medicament, stored between the closure and the piston, through such an injection unit;

a threaded piston rod coupled non-rotatably to an element which has a cross section corresponding to, and which is disposed in, the non-circular interior portion of the ampoule so as to be guided non-rotatably in such interior portion;

a nut having an inner thread engaging the thread of the piston rod; and a stop against which the nut abuts prior to setting a dose to prevent movement of the piston rod toward the first end of the ampoule, wherein the nut may be rotated about the piston rod, to move away from the stop, in order to set a dose, and wherein, after setting a dose, the piston rod may be moved toward the ampoule's first end to force the piston into the ampoule.

2. A device according to claim 1, wherein the stop is formed by the second end of the ampoule, and wherein the nut has a diameter enabling it to abut against the second end of the ampoule.

3. A device according to claim 1, wherein said element is a pressure foot which acts on the piston.

4. A cylinder ampoule according to claim 1, wherein said element is the piston itself.

5. A cylinder ampoule according to claim 1, wherein the ampoule forms a syringe housing.

* * * * *